(12) United States Patent
Choudary et al.

(10) Patent No.: US 6,239,302 B1
(45) Date of Patent: May 29, 2001

(54) PROCESS FOR THE PREPARATION OF ACYLFERROCENES

(75) Inventors: Boyapati Manoranjan Choudary; Konatham Saidi Reddy; Mannepalli Lakshmi Kantam; Kondapuram Vijaya Raghavan, all of Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/545,275

(22) Filed: Apr. 7, 2000

(51) Int. Cl.$^7$ .................................................. C07F 17/02
(52) U.S. Cl. ................................ 556/145; 502/80; 502/84
(58) Field of Search .............................. 556/145; 502/80, 502/84

(56) References Cited

U.S. PATENT DOCUMENTS

| | | | | |
|---|---|---|---|---|
| 2,852,542 | * | 9/1958 | Sweeney | 260/429 |
| 2,875,223 | * | 2/1959 | Pedersen et al. | 260/439 |
| 2,988,562 | * | 6/1961 | Weinmayr | 260/439 |
| 3,036,106 | * | 5/1962 | Leigh | 260/439 |
| 3,957,841 | * | 5/1976 | Nesmeyanov et al. | 260/439 CY |

* cited by examiner

*Primary Examiner*—Porfirio Nazario-Gonzalez
(74) *Attorney, Agent, or Firm*—McDonnell Boehnen Hulbe & Berghoff

(57) ABSTRACT

The invention relates to a process for the preparation of acylferrocenes from a ferrocene using a montmorillonite or a metal ion exchanged K10 montnorillonite clay catalyst.

10 Claims, No Drawings

PROCESS FOR THE PREPARATION OF ACYLFERROCENES

BACKGROUND OF THE INVENTION

1. Field of the Invention

The present invention relates to an improved process for the preparation of acylferrocenes from ferrocenes using acid anhydrides as acylating agents and montmorillonite clays as catalysts.

2. Summary of the Related Art

Acylferrocenes are important intermediates for the production of varied functional materials such as functional polymers, surfactants, charge transfer complexes, ion sensors, masking agents, coupling agents, chiral catalysts, combustion catalysts for propellants, and the like. Acylferrocenes are also employed as a medicament for the treatment of sideropenia symptoms and sideropenic anemia (anemia caused by repeated bloodletting).

Friedel-Crafts acylation of ferrocene with acyl halides leads to the formation of acylferrocenes. Ferrocene is $10^6$ times more reactive than benzene in acylation. They are generally prepared by reacting ferrocene with acetic anhydride/acyl chlorides in the presence of a Lewis acid such as aluminium chloride or polyphosphoric acid. It has been found that both acylferrocenes and diacylferrocenes can be prepared in satisfactory yields by varying the ratios of ferrocene and/or acid chloride, and by altering the mode of addition as well. Monoacylferrocenes are prepared by the drop-wise addition of the acid chloride-aluminium chloride complex to the ferrocene solution, using equimolar amounts of acid chloride, catalyst and ferrocene. The diacylferrocenes are prepared by adding ferrocene solution to the complex using a molar ratio of >2:1 of both the acid chloride and aluminium chloride to ferrocene.

Rosenblum and Woodward, *J. Am. Chem. Soc.*, 80 5443, (1958) discloses the preparation of acylferrocenes by the reaction of ferrocene with acetyl chloride in the presence of stoichiometric quantities of aluminum chloride. "Vogels Textbook of Practical Organic Chemistry", $5^{th}$ Edition, 1014 (1989) teaches the preparation of acylferrocene by the reaction of ferrocene with acetic anhydride in the presence of 85% phosphoric acid.

Furthermore, British Patent Nos. BP 869504 and BP 819108 disclose the reaction of ferrocene with an appropriate acid chloride or anhydride under Friedel-Crafts conditions in the presence of Lewis acids such as aluminium chloride, boron trifluoride, hydrogen fluoride or polyphosphoric acid in solvents such as carbon disulfide, ethers, nitromethane or ethylene chloride. The drawbacks in these processes are that when aluminium chloride is used, diacyl compounds are usually obtained, whereas in the presence of hydrogen fluoride or polyphosphoric acid, monoacyl compounds are produced. Other drawbacks are the use of stoichiometric quantities of hazardous aluminium chloride or phosphoric acid and tedious work-up procedures.

It is thus necessary to find a novel process for making acylferrocenes that eliminates the use of the corrosive Lewis acids such as aluminum chloride. It is further desirable to find such a process that is more economical and more selective towards a particular product.

SUMMARY OF THE INVENTION

The present invention provides an improved process for the preparation of acylferrocenes from ferrocenes using acid anhydrides as acylating agents and montinorillonite clays as catalysts. More particularly, the present invention eliminates the need of employing corrosive and toxic acyl chlorides and Lewis acids (e.g. aluminium chloride, polyphosphoric alcid, boron trifluoride and hydrogen fluoride) by utilizing an eco-friendly process for the preparation of acylferrocenes from ferrocenes using acid anhydrides as acylating agents and montinorillonite clays as catalysts. The process of the present invention totally eliminates the formation, and thus the need to dispose of, salts formed in traditional Friedel-Crafts acylations.

It is therefore an object of the invention to provide a process for the preparation of acylferrocenes that is highly selective and substantially quantitative.

It is further an object of the invention to provide a process for the preparation of acylferrocenes that has a shorter duration as well as a simple work-up procedure.

It is another object of the invention to provide a process for the preparation of acylferrocenes in which economical and safe clays are used as catalysts in place of a Lewis acid. The present process envisages no disposal problem as the catalyst can be used for several cycles.

The invention offers excellent yields, greater selectivity towards monoacyl ferrocenes, and almost negligible effluents. The invention thus offers advantages over the prior art processes utilizing hazardous Lewis acids as catalysts. Therefore, the process described in this invention is technically feasible, economically viable and environmentally friendly.

DETAILED DESCRIPTION OF THE INVENTION

The invention relates to a process for the preparation of acylferrocenes employing commercially available montmorillonite and various metal ion exchanged acid catalysts for effecting acylation. The invention relates to the use of commercially available K10 montmorillonite and various metal ion exchanged K10 montmorillonites as solid acid catalysts for effecting acylation of ferrocenes with acid anhydrides as acylating agents. The invention offers excellent yields, greater selectivity towards monoacyl ferrocenes, and almost negligible effluents.

Accordingly, an embodiment of the present invention provides for a process for the preparation of acylferrocenes comprising reacting a ferrocene with an acid anhydride acylating agent in the presence of a montmorillonite or metal ion exchanged K10 montmorillonites clay catalyst in a solvent at a temperature in the range of about 60 to 165 deg celcius for a period of 3 to 8 hrs and recovering the acylferrocenes by conventional methods.

By "ferrocene" in the present invention is meant dicyclopentadienyliron as depicted by formula I:

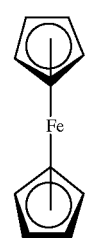

I

By "acid anhydride" in the present invention is meant a compound of the formula $(RCO)_2O$ wherein R is lower alkyl or each R is connected to the other R such that, together with the carbonyl group to which each R attached, a carbocyclic ring is formed. In a preferred embodiment, the acylating agent is selected from the group of acid anhydrides having from 2 to 7 carbon atoms. Examples of preferred acid anhydrides for purposes of the present invention include, but are not limited to, acetic anhydride, propionic anhydride, butyric anhydride, valeric anhydride, hexanoic anhydride and heptanoic anhydride.

By "lower alkyl" in the present invention is meant straight or branched chain alkyl groups or cycloalkyl groups having 1–10 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl, cyclopropyl, cyclopropylmethyl, and the like.

By "carbocyclic ring" is meant a saturated or aromatic hydrocarbon ring having a single ring (e.g., phenyl or cyclopentyl), multiple rings (e.g., biphenyl), or multiple condensed rings.

Suitable solvents for the present invention include, but are not limited to, (un)substituted hydrocarbon solvents such as, for example, chlorobenzene, acetonitrile or nitromethane. Another suitable solvent for the present invention is the acid anhydride itself. Acetic anhydride is a typical example where the acylating reagent can also act as the solvent. Preferred solvents of the present invention are chlorobenzene or acetic anhydride.

In yet another embodiment, the montmorillonitelmetal ion exchanged K10 montmorillonites clay catalyst is selected from $Co^{2+}$, $Z^{2+}$, $Al^{3+}$, $Ce^{3+}$, $La^{3+}$, or $Zr^{4+}$-montmorillonites. The amount of the catalyst used is from between 5 to 50% by weight with respect to the substrate charged. The catalyst is commercially available as, for example, K10 montmorillonite and various metal ion exchanged K10 montmorillonites as solid acid catalysts.

In acid treated montmorillonite, K10, the density of the Bronsted acidic sites increases because of increased number of broken edges resulting from the disruption of stacked layers in natural montmorillonite, while the Lewis acidity decreases due to desorption of metal ion inherently present in natural montmorillonite during acid treatment. K10 montmorillonite with very high Bronsted acidity thus induces the acylation as exemplified above. Introduction of transition metals in montmorillonite K10 by exchange process increases the Lewis acidity of the material and simultaneously decreases Bronsted acidity. The efficacy of various modified montmorillonites is in the order of zeolite<$Cu^{2+}$ mont.<$Fe^{3+}$ mont.<$Zn^{2+}$ mont.<FePILC-K10 mont. in acylation of ferrocenes. This result indicates the higher density of acidic sites, i.e., Bronsted sites in K10 montmorillonite or Lewis sites in FePILC-K10 induces the acylation of ferrocenes. All the metal ion-exchanged K10 montmorillonite catalysts were prepared as described in example 1 and employed in the acylation of ferrocenes with acid anhydrides as acylating agents as described in the examples.

In another embodiment of the invention, the catalyst was subjected to 4 or more recycles, displaying consistent activity with each reaction.

In a preferred embodiment, the reaction is conducted at a temperature in the range of from between 120 to 165° C. for 2–12 hrs. In a more preferred embodiment, the reaction is conducted at temperatures ranging from between 125–135° C. for 4–10 hours.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

EXAMPLES

Example 1

A series of catalysts were prepared as described below. The acylation of ferrocenes with acetic anhydride of different catalysts is provided in Table 1. Table 2 details the conversion of ferrocene to acylferrocene in % employing different acylating agents.

A) K10 montmorillonite (obtained from mls. Fluka, a Sigma Aldrich company, Switzerland) was used as such.

B) Metal exchanged montmorillonites:

$Fe^{3+}$ exchanged montmorillonite: 80 g of K10 montmorillonite (obtained from M/s. Fluka, a Sigma Aldrich Company, Switzerland) was added to a 1 liter aqueous solution of $FeCle_3$ (1.0 M) under stirring. Stirring was maintained for 16–30 h in order to saturate the exchange capacity of K10 montmorillonite. The clay suspension was centrifuged and the supernatant solution was discarded. Washing cycles were repeated until the disappearance of Cl— ions from the discarded water. The clay was dried overnight in an oven at 120° C. and finally ground in a mortar.

Other metal exchanged clays such as $Cu^{2+}$, $Co^{2+}$, $Zn^{2+}$ $Al^{3+}$, $Ce^{3+}$, $La^{3+}$, or $Zr^{4+}$-montmorillonite catalysts were prepared in a similar procedure by dissolving the corresponding metal salts.

C) FePILC from KIO montmorillonite: (FePILC-K10 Iron pillared clay):

The Na-montmorillonite was prepared by suspending and stirring commercial montmorillonite in excess aqueous sodium chloride-solution for 24 h. The Na-montmorillonite was separated by centrifugation and washed free of chloride ions by deionized water and air-dried. The cation exchange capacity of the air-dried clay is 0.8 equi.

Trinuclear acetato-hydroxy-iron (III) nitrate: $Fe_3$ $(OCOCH_3)_7OH.2H_2O$ $NO_3$ was used as the cation source for exchanging with the Na-montnorillonite. 80.8 g of $Fe(NO_3)_3.5H_2O$ was dissolved in 50 ml of ethyl alcohol. The solution was reacted with 140 ml of acetic anhydride, producing the evolution of heat. The solution was then cooled in an ice bath and the resulting precipitate was separated and used without further purification in the pillaring procedure.

Cation exchange: A 0.04 M aqueous solution of trinuclear acetato-hydroxy-iron (III) nitrate (19.48 g) in 700 ml of water was added to stirred 1% Na-montmorillonite aqueous suspension (8 g of Na-mont. in 800 ml of water). The mixture was stirred for 3 hours at 40° C., separated by centrifugation, washed with water several times to remove excess iron ions and dried to get FePILC-K10.

Example 2

Ferrocene (1 mmol, 0.186 g) acetic anhydride (1 ml, 10 mmol) and chlorobenzene (10 ml) were heated at reflux temperature in a R.B flask (50 ml) in presence of K10 montmorillonite catalyst (0.200 g). After completion of the reaction (followed by TLC), the reaction mixture was filtered and concentrated on a rotovap to obtain the crude product. The crude product was subjected to flash chromatography to afford acylated product (0.193 g).

Example 3

Ferrocene (1 mmol, 0.186 g), acetic anhydride (1 ml, 10 mmol) and chlorobenzene (10 ml) were heated at reflux temperature in a round bottom flask (50 ml) in the presence of $Fe^{3+}$ exchanged montmorillonite catalyst (0.200 g). After completion of the reaction (followed by TLC), the reaction mixture was filtered and concentrated on rotovap to obtain the crude product. The crude product was subjected to flash chromatography to afford acylated product (0.134 g).

Example 4

Ferrocene (1 mmol, 0.186 g), acetic anhydride (1 ml, 10 mmol) and chlorobenzene (10 ml) were heated at reflux temperature in a round bottom flask (50 ml) in presence of $Zn^{2+}$-montmorillonite catalyst (0.200 g). After completion of the reaction (followed by TLC), the reaction mixture was filtered and concentrated on rotovap to obtain the crude product. The crude product was subjected to flash chromatography to afford acylated product (0.134 g).

Example 5

Ferrocene (1 mmol, 0.186 g), acetic anhydride (1 ml, 10 mmol) and chlorobenzene (10 ml) were heated at reflux temperature in a round bottom flask (50 ml) in presence of $CU^{2+}$ montmorillonite catalyst (0.200 g). After completion of the reaction (followed by TLC), the reaction mixture was filtered and concentrated on rotovap to obtain the crude product. The crude product was subjected to flash chromatography to afford the pure product (0.114 g).

Example 6

Ferrocene (1 mmol, 0.186 g), acetic anhydride (1 ml, 10 mmol) and chlorobenzene (10 ml) were heated at reflux temperature in a round bottom flask (50 ml) in presence of Fe-pillared K10 montmorillonite catalyst (0.200 g). After completion of the reaction (followed by TLC), the reaction mixture was filtered and concentrated on rotovap to obtain the crude product. The crude product was subjected to flash chromatography to afford acylated product (0.162 g).

Example 7

Ferrocene (1 mmol, 0186 g)acetic anhydride(1 ml, 10 mmol) and chlorobenzene (10 ml) were heated at reflux temperature in a round bottom flask (50 ml) in presence of zeolite catalyst (0–200 g). After completion of the reaction (followed by TLC), the reaction mixture was filtered and concentrated on rotovap to obtain the crude product. The crude product was subjected to flash chromatography to afford acylated product (0.112 g).

Example 8

Ferrocene (1 mmol, 0.1 86 g), acetic anhydride (2 mmol) and chlorobenzene (3 ml) were heated at reflux temperature in a Schlenk flask (5 ml) in presence of K10 montmorillonite catalyst (0.093 g). After completion of the reaction (followed by TLC), the reaction mixture was filtered and concentrated on rotovap to obtain the crude product. The crude product was subjected to flash chromatography to afford acylated product (0.134 g).

Example 9

Ferrocene (1 mmol, 0.186 g), propionic anhydride (2 mmol) and chlorobenzene (3 ml) were heated at reflux temperature in a Schlenk flask (5 ml) in presence of K10 montmorillonite catalyst (0.093 g). After completion of the reaction (followed by TLC), the reaction mixture was filtered and concentrated on a rotovap to obtain the crude product. The crude product was subjected to flash chromatography to afford the pure product (0.194 g).

Example 10

Ferrocene (1 mmol, 0.186 g), butyric anhydride (2 mmol) and chlorobenzene (3 ml) were heated at reflux temperature in a Schlenk flask (5 ml) in presence of K10 montmorillonite catalyst (0.093 g). After completion of the reaction (followed by TLC), the reaction mixture was filtered and concentrated on a rotovap to obtain the crude product. The crude product was subjected to flash chromatography to afford the pure product (0.204 g).

Example 11

Ferrocene (1 mmol, 0.186 g) and valeric anhydride (2 mmol) and chlorobenzene (3 ml) were heated in reflux temperature in a Schlenk flask (5 ml) in presence of K10 montmorillonite catalyst (0.093 g). After completion of the reaction (followed by TLC), the reaction mixture was filtered and concentrated on a rotovap to obtain the crude product. The crude product was subjected to flash chromatography to afford the acylated product (0.217 g).

Example 12

Ferrocene (1 mmol, 0.186 g) and hexanoic anhydride (2 mmol) and chlorobenzene (3 ml) were heated at reflux temperature in a Schlenk flask (5 ml) in presence of K10 montmorillonite catalyst (0.093 g). After completion of the reaction (followed by TLC) the reaction mixture was filtered and concentrated on a rotovap to obtain the crude product. The crude product was subjected to flash chromatography to afford the acylated product (0.220 g).

Example 13

Ferrocene (1 mmol, 0.186 g) and acetic anhydride (2.5 ml) were heated to reflux temperature in a Schlenk flask (5 ml) in presence of K10 montmorillonite catalyst (0.047 g). After completion of the reaction (followed by TLC), the reaction mixture was filtered and the excess anhydride was recovered by distillation to obtain the crude product. The crude product was subjected to flash chromatography to afford acylated the product (0.207 g).

Example 14

Ferrocene (1 mmol, 0.186 g) and propionic anhydride (2.5 ml) were stirred at an oil bath temperature of 165° C. in a Schlenk flask (5 ml) in presence of K10 montmorillonite catalyst (0.047 g). After completion of the reaction (followed by TLC), the reaction mixture was filtered and the excess anhydride by was recovered distillation to obtain the crude product. The crude product was subjected to flash chromatography to afford acylated product (0.210 g).

Example 15

Ferrocene (1 mmol, 0.186 g) and butyric anhydride (2.5 ml) were stirred at an oil bath temperature of 165° C. in a Schlenk flask (5 ml) in the presence of K10 montmorillonite catalyst (0.047 g). After completion of the reaction (followed by TLC) the reaction mixture was filtered and the excess anhydride was recovered by distillation to obtain the crude product. The crude product was subjected to flash chromatography to afford acylated product (0.230 g).

Example 16

Ferrocene (1 mmol, 0.186 g) and valeric anhydride (2.5 ml) were stirred at an oil bath temperature of 165° C. in a Schlenk flask (5 ml) in presence of K10 montmorillonite catalyst (0.047 g). After completion of the reaction (followed by TLC), the reaction mixture was filtered and the excess anhydride was recovered by distillation to obtain the crude product. The crude product was subjected to flash chromatography to afford the acylated product (0.240 g).

Example 17

Ferrocene (1 mmol, 0.186 g) and hexanoic anhydride (2.5 ml) were stirred at an oil bath temperature of 165° C. in a Schlenk flask (5 ml) in the presence of K10 montmorillonite catalyst (0.047 g). After completion of the reaction (followed by TLC), the reaction mixture was filtered and the excess anhydride was recovered by distillation to obtain the crude product. The crude product was subjected to flash chromatography to afford the acylated product (0.250 g).

Example 18

Ferrocene (10 mmol, 1.86 g) and acetic anhydride (25 ml) were heated to reflux in a Schlenk flask (50 ml) in the presence of K10 montmorillonite catalyst (0.470 g). After completion of the reaction (followed by TLC), the reaction mixture was filtered and the excess anhydride was recovered by distillation to obtain the crude product. The crude product was subjected to flash chromatography to afford the acylated products (2.00 g).

The acylation of ferrocenes with acetic anhydride by different catalysts is provided in Table 1. Table 2 provides the conversion in % on acylation of ferrocene with different acylating agents.

TABLE 1

Acylation of ferrocenes with acetic anhydride by different catalysts

| S No. | Example[a] | Catalyst | Time (h) | Conversion[b] (%) |
|---|---|---|---|---|
| 1 | 2 | K10 mont. | 8 | 85 |
| 2 | 3 | $Fe^{3}$-exchanged mont. | 24 | 60 |
| 3 | 4 | $Zn^{2}$-exchanged mont. | 24 | 62 |
| 4 | 5 | $Cu^{2+}$-exchanged mont. | 24 | 53 |
| 5 | 6 | FePILC-K10 | 24 | 75 |
| 6 | 7 | Zeolite | 24 | 52 |

[a]As exemplified in the text
[b]From NMR. Yields based on ferrocene

TABLE 2

Acylation of Ferrocene

| Example No.[a] | Solvent | Acylating Agent | Temp. (° C.) | Conversion[b] [%] | Selectivity[c] [%] mono- | di- |
|---|---|---|---|---|---|---|
| 8 | chlorobenzene | acetic anhydride | 150–155 | 62 | 96 | 4 |
| 9 | chlorobenzene | propionic anhydride | 150–155 | 85 | 97 | 3 |
| 10 | chlorobenzene | butyric anhydride | 150–155 | 84 | 96 | 4 |
| 11 | chlorobenzene | valeric anhydride | 150–155 | 85 | 97 | 3 |
| 12 | chlorobenzene | hexanoic anhydride | 150–155 | 82 | 97 | 3 |
| 13 | acetic anhydride | acetic anhydride | 150–155 | 96 | 96 | 4 |
| 14 | propionic anhydride | propionic anhydride | 165 | 92 | 98 | 2 |
| 15 | butyric anhydride | butyric anhydride | 165 | 95 | 98 | 2 |
| 16 | valeric anhydride | valeric anhydride | 165 | 94 | 98 | 2 |
| 17 | hexanoic anhydride | hexanoic anhydride | 165 | 93 | 98 | 2 |
| 18 | acetic anhydride | acetic anhydride | 165 | 92 | 97 | 3 |

[a]As exemplified in the text.
[b]From NMR; yields based on ferrocene (mono- and di- acylated).
[c]Based on NMR.

The invention and the manner and process of making and using it, are now described in such fill, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A process for the preparation of acylferrocenes comprising reacting a ferrocene with an acid anhydride acylating agent in a solvent in the presence of a catalyst selected from the group consisting of a montmorillonite clay catalyst and a metal ion exchanged K10 montmorillonite clay catalyst.

2. A process according to claim 1 wherein the acid anhydride has from 2 to 7 carbon atoms.

3. A process according to claim 2 wherein the acid anhydride is selected from the group consisting of acetic anhydride, propionic anhydride, butyric anhydride, valeric anhydride, hexanoic arhydride and heptanoic anhydride.

4. A process according to claim 1 wherein the montmorillonite/metal ion exchanged K10 montmorillonites clay catalyst is selected from $Co^{2+}$, $Zn^{2+}$, $Al^{3+}$, $Ce^{3+}$, $La^{3+}$, and $Zr^{4+}$ montmorillonites.

5. A process according to claim 1 wherein the solvent is a substituted hydrocarbon.

6. A process according to claim 1 wherein the solvent is the acid anhydride.

7. A process according to claim 5 wherein the substituted hydrocarbon solvent is chlorobenzene.

8. A process according to claim 1 wherein the reaction is run at a temperature in the range of from between 80 to 165° C.

9. A process according to claim 8 wherein the reaction is run at a temperature in the range of from between 120 to 165° C.

10. A process according to claim 9 wherein the reaction is run from between 3 to 8 hours.

* * * * *